United States Patent [19]

Rappaport

[11] 4,450,591
[45] May 29, 1984

[54] INTERNAL ANTI-PRORATORY PLUG ASSEMBLY AND PROCESS OF INSTALLING THE SAME

[76] Inventor: Mark J. Rappaport, 555 Wyncourtney Dr., Atlanta, Ga. 30328

[21] Appl. No.: 329,186

[22] Filed: Dec. 10, 1981

[51] Int. Cl.³ .............................................. A61F 1/00
[52] U.S. Cl. ...................................... 3/1.9; 128/92 C
[58] Field of Search ............ 128/92 C, 92 CA, 92 G, 128/92 R, 92 B, 92 E; 3/1, 1.9, 1.91

[56] References Cited
U.S. PATENT DOCUMENTS 3,745,590  7/1973  Stubstad .................................. 3/1.9
3,973,277  8/1976  Semple et al. ............................. 3/1
4,149,277  4/1979  Bokros ..................................... 3/1.9
4,344,190  8/1982  Lee et al. ......................... 128/92 C X Primary Examiner—Richard J. Apley
Assistant Examiner—David J. Isabella
Attorney, Agent, or Firm—Newton, Hopkins & Ormsby

[57] ABSTRACT

A truncated unitary plastic cone shaped plug is provided with a tie line, the ends of which protrude from the minor base of the plug and are tied together around the deltoid ligament after insertion of the plug into the sinus tarsus or opening of the subtalar joint of a person in a subtalar arthroereisis operation to correct pes plano valgus.

3 Claims, 6 Drawing Figures

INTERNAL ANTI-PRORATORY PLUG ASSEMBLY AND PROCESS OF INSTALLING THE SAME

BACKGROUND OF THE INVENTION

1. Field of the Invention

This invention relates to an internal anti-proratory plug assembly and to a process of installing the same in a person to correct pes plano valgus.

BACKGROUND

In the past, it has been common practice to insert a plug of some type into the sinus tarsus or below the subtalar joint at the ankle of a person so as to attempt to correct or modify the angle between the leg and foot of a person.

LaLievre J. in *Current Concepts and Correction in the Valgus Foot*, p. 43, Clinical Orthopedics 70, 1970, in 1970, reported his findings on 80 cases, including children from 3-6 years old in which the heel was held vertical with a staple across the subtalar joint. In the adults a homogenous bone graft was driven into the tarsal sinus but was not fixated in order to maintain foot flexibility. In this study the youngest patient was 2 and the oldest was 96. He stated that pain on ambulation was abolished in all the patients studied with excellent results in 73 of the 80 cases, during the 11 year period. The remaining 7 patients had esthetically poor results due primarily to cosmesis.

Subotnick, S. in *The Subtalar Joint Lateral Extra Articular Arthoereisis,* p.3, J.A.P.A. 67, 1977, in 1976, reported on 14 children from 1½ to 17 years old in which the procedure was performed, nine of which were bilateral. Two cases were in combination with a Kidner type procedure, and two others were unilateral subtalar arthroereisis with a Kidner-Young performed on the contra-lateral foot. He stated the procedure had little morbity and the average calcaneal valgus angle changed from 18° to 6° postoperatively with a 3 year followup.

Lanham, R. in *Indications and Compications of Arthroereisis in Hypermobile Flat Foot,* p.3, J.A.P.A. 69, 1979, reported randomly sampling 11 of 51 cases of varying ages that were assessed radiographically. Four radiographic measurements were taken from the dorsal-plantar and lateral x-rays of the foot. These measurements were talar declination angle, talocalcaneal (Kites angle), lateral talocalcaneal angle, and calcaneal inclination angle. Postoperatively he reported that in 15 of 22 (68%) the talar declination angle and the lateral talocalcaneal angle decreased. Also, in 13 of 22 feet (59%) Kites angle decreased postoperatively. These researchers were apparently encouraged with these results in light of the relative simplicity of the procedure.

Additional prior art includes DiGiovanni, J. E. and Smith, S. D.: *Normal Biomechanics of the Adult Rearfoot,* p. 11, J.A.P.A. 66, 1976; Root, M. L., Weed, J. H., Orien, W. P.: *Biomechanical Examination of the Foot,* Clinical Biomechanic Corporation, Los Angeles, California, 1971; Root, M. L., Orien, W. P., Weed, J. H.: *Normal and Abnormal Functions of the Foot,* Clinical Biomechanics Corporation, Los Angeles, California, 1977; Grice, D. S.: *An Extra-Articular Arthrodesis of the Subastragular Joint for Correction of Paralytic Flat Feet in Children,* p. 927, J. Bone Joint Surgery 34-A, 1952; Grice, D. S.: *The Role of Subtalar Fusion and the Treatment of Valgus Deformities of Feet,* p. 127, American Academy of Orthopedic Surgery 16, 1959.

SUMMARY OF THE INVENTION

Briefly described, the apparatus of the present invention includes a truncated, unitary, plastic, cone shaped plug provided with a pair of outwardly protruding tie lines or sutures which extend from the minor base of the plug. The plug is inserted into the sinus tarsus or opening in the subtalar joint in a subtalar arthroereisis operation to correct the pes plano valgus in a primate, namely a person. The operation is usually to be performed on younger persons from 18 months old to 14 years old and preferrably 4 years old.

In the operation, a plug of an appropriate size is provided by having several different sizes of plugs available and after exposing the sinus tarsus, by trial and error determining the proper plug to be employed which limits calcaneal eversion to 0°. A line having its central bight embedded in the plug provides a pair of ends which are threaded through the sinus tarsus and passed outwardly and around the deltoid ligament. The two ends of the line are then tied outwardly of the ligament so as to yieldably hold the plug in place in the sinus tarsus.

Accordingly, it is an object of the present invention to provide an internal anti-proratory plug assembly which is readily and easily installed in the sinus tarsus and will not readily be dislodged therefrom with continued use.

Another object of the present invention is to provide a process by which flat foot can be corrected in a person.

Other objects, features and advantages of the present invention will become apparent from the following description when taken in conjunction with the accompanying drawing wherein like characters of reference designate corresponding parts throughout the several views.

DESCRIPTION OF THE PREFERRED EMBODIMENTS

Figure 1:
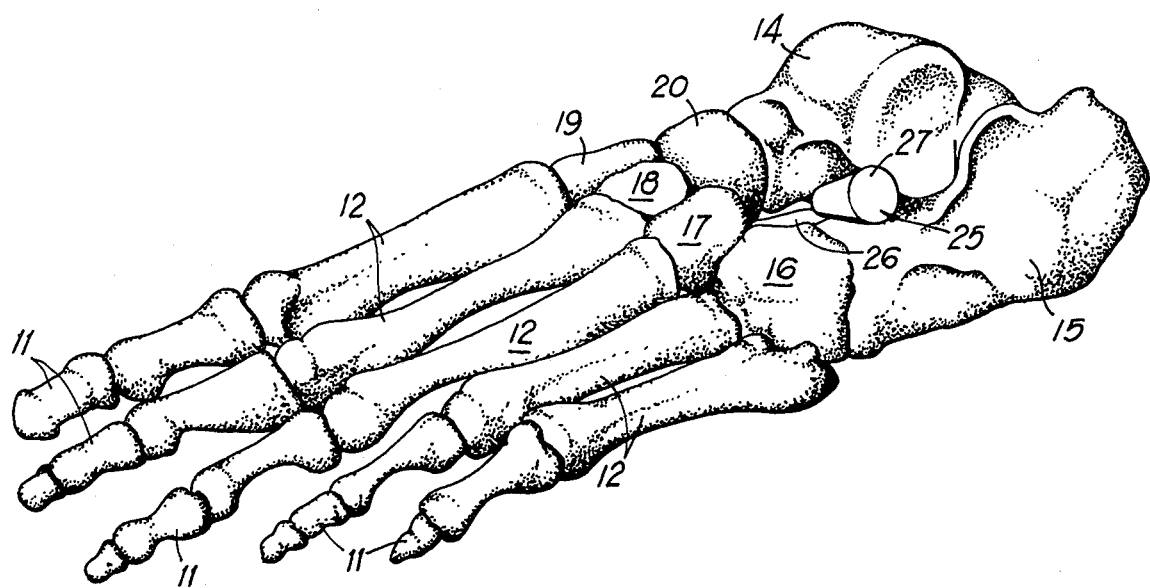
FIG. 1 is a perspective skeletal view of a persons foot having installed therein the anti-proratory plug assembly of the present invention.
Figure 2:
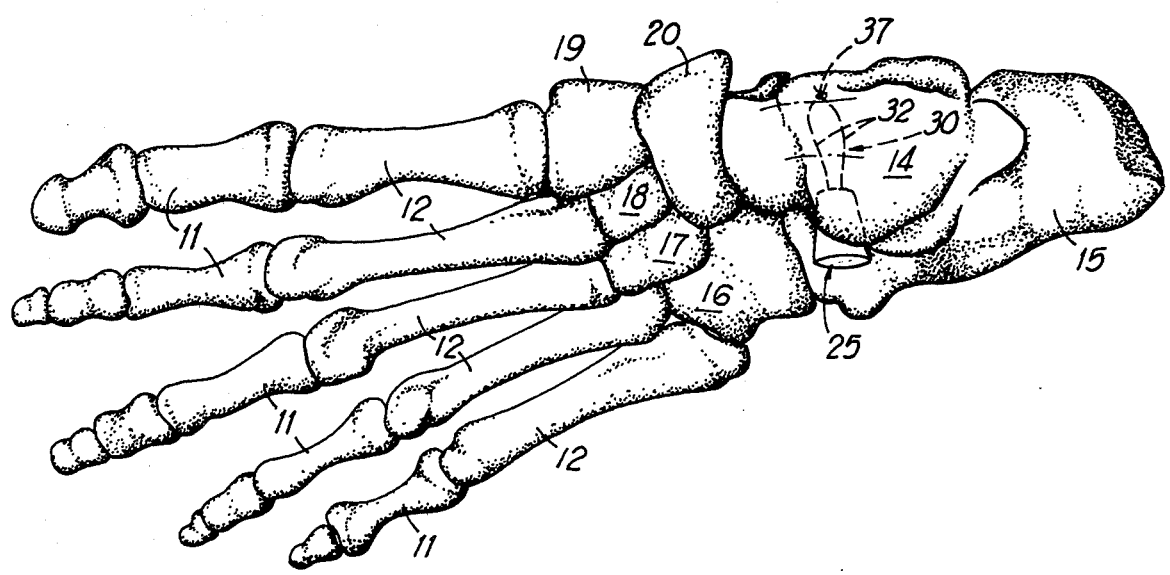
FIG. 2 is a top plan view of the skeletal foot depicted in FIG. 1.

Referring now in detail to the drawings, in FIG. 1 and 2, the skeletal foot of a person is denoted generally by the numeral 10. It will be recognized that the foot 10 has fourteen phalanges or toe bones 11 connected to the metatarsus bones 12. There are also seven tarsal bones, of which the talus 14 supports the leg bone (not shown) and the calcaneus or heel bone 15 are the largest and are adjacent to each other. The other tarsal bones include the navicular 20, three cuneiforms 17, 18 and 19 and the cuboid 16 between the metatarsals bones 12 and the navicular 20.

According to the present invention, I prepare a truncated cone shaped, unitary, semi-rigid, plastic (silicon)

plug 25 which has the frusto-conical shape of a cork bottle stopper, the plug 25 being produced in various sizes to be received in the various sizes of the sinus tarsus or subtalar opening 26, in FIG. 1, between the talus 14 and the calcaneus 15.

Figure 3:
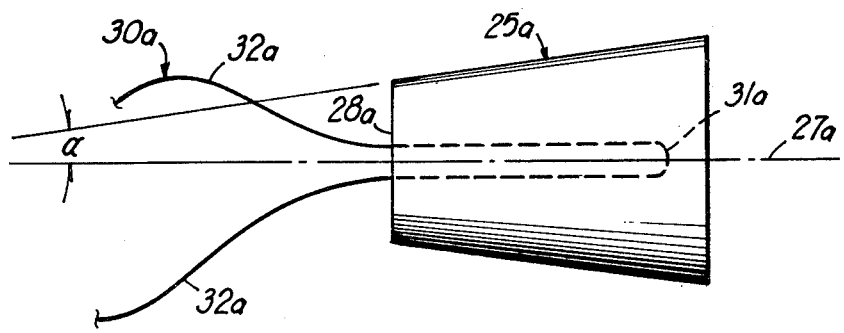
FIG. 3 is a side elevational view of one of the plug assemblies constructed in accordance with the present invention.
Figure 4:
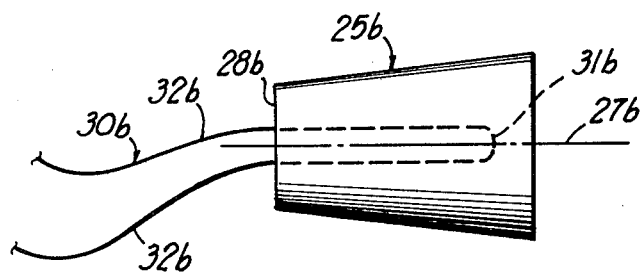
FIGS. 4, 5 and 6 are views of additional but different size plug assemblies also constructed in accordance with the present invention.
Figure 5:
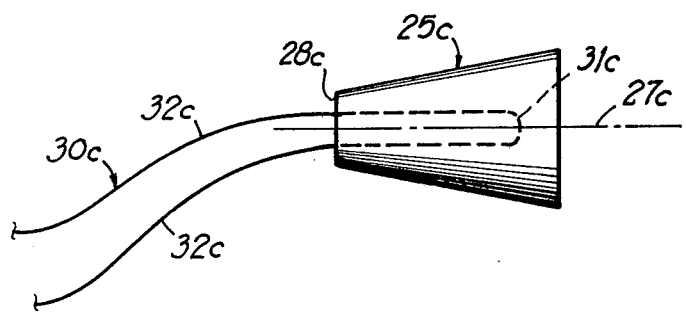
Figure 6:
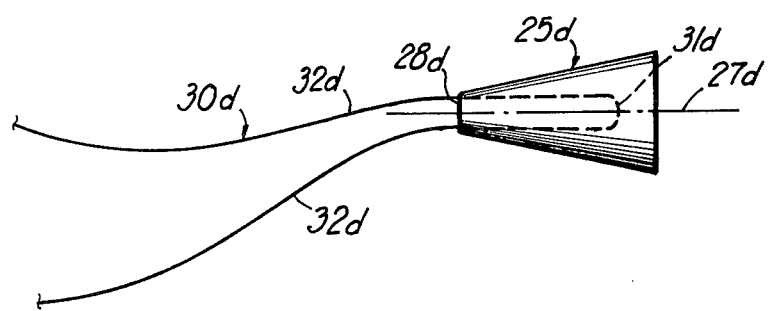

In FIGS. 3, 4, 5 and 6 the various size plugs, which can be employed as the plug 25 above, are depicted in more detail, these plugs being designated respectively by the numerals 25a in FIG. 3, 25b in FIG. 4, 25c in FIG. 5 and 25d in FIG. 6. Plugs 25a, 25b, 25c and 25d are symetrical about their respective longitudinal axes 27a, 27b, 27c and 27d. At the outer ends of the plugs 25, 25a, 25b, 25c and 25d, there are respectively flat, radially extending, major, circular bases 27, 27a, 27b, 27c and 27d and at their other or inner ends there are respectively, flat, radially extending, minor, circular bases 28, 28a, 28b, 28c and 28d. The conical side walls 29, 29a, 29b, 29c and 29d taper uniformly respectively from the peripheries of bases 27, 27a, 27b, 27c and 27d to the peripheries of bases 28, 28a, 28b, 28c and 28d.

Each of the side walls 29, 29a, 29b, 29c and 29d has a taper at an angle a with respect to its longitudinal axis, such as axis 27a, 27b, 27c or 27d, as the case may be. The respective dimensions of each of the preferred plugs 25a, 25b, 25c and 25d are found in Table I.

TABLE I

| PLUG | LENGTH | | DIAMETER OF LARGE BASE | | DIAMETER OF SMALL BASE | ANGLE a |
|---|---|---|---|---|---|---|
| 25a | 2.00 cm | 27a | 1.5 cm | 28a | 1.0 cm | 7° |
| 25b | 1.75 cm | 27b | 1 25 cm | 28b | .75 cm | 8° |
| 25c | 1.5 cm | 27c | 1.0 cm | 28c | .5 cm | 9° 20' |
| 25d | 1.25 cm | 27d | .75 cm | 28d | .25 cm | 11° 10' |

Embedded respectively in the plugs 25, 25a, 25b, 25c and 25d adjacent to their associated major bases 27a, 27b, 27c and 27d are the bights, such as bights 31a 31b, 31c and 31d, at the mid portions of the flexible securing lines or sutures 30, 30a, 30b, 30c and 30d. The end portions of these lines 30, 30a, 30b, 30c and 30d pass from the bights, such as bights 30a, 30b, 30c, 30d, axially through a major portion of each associated plug and then outwardly through the central portion of respective minor bases 28, 28a, 28b, 28c and 28d to provide the ends 32, 32a, 32b, 32c and 32d.

The lines 30, 30a, 30b, 30c, 30d are preferrably 2-0 sutures, known in the market as TEVDEK, a product of Dek natel Green Braided Tevdek II, Queens Village, New York, 11329 and the plugs 30, 30a, 30b, 30c and 30d are preferrably formed of silicon, known in the market as SILASTIC, a product of Dow Corning Corporation, Medical Products Division, Midland, Michigan 48640.

The procedure of installing a plug, such as plug 30, 30a, 30b, 30c and 30d is similar to that described by Lanham with some significant modifications. General anesthesia is employed on all cases and local hemostasis is obtained utilizing a local anesthetic containing epinephrine.

A linear incision is made over the sinus tarsi after having carefully palpated the central dell. The incision follows the skin lines and runs from the dorsal intermediate cutaneous nerve to the peroneal tendons. The incision is carried through the subcutaneous tissue which requires cutting and ligating several vessels.

The inferior extensor retinaculum is then encountered and transected parallel with the skin incision and the borders of the tarsal sinus are then palpated bluntly.

The capsule is then incised and retracted and the fat plug is removed. The posterior facet is always readily visible and the floor and the ceiling of the tarsal sinus are of relatively soft bone. Therefore, it is strongly recommended that a small Metsenbaum scissors be used rather than a scalpel for dissection of the fat plug. This mitigates the insult on the articular cartilage and friable bone.

Once the fat plug is removed the scissors are inserted horizontally into the sinus tarsi and moved medially and anteriorly, transecting the talo-calcaneo ligament. This procedure is extremely important because once the ligament is cut one can immediately detect an increase in supination of the calcaneus 15.

Prior to initiating surgery, plugs 30a, 30b, 30c and 30d of each size should be available. The exact size is selected by trial placement of plugs in the sinus tarsus until the proper size plug is selected which will limit calcaneal eversion to 0°. A portion of the major base of a plug can be removed, if desired. The plug selected has a transverse dimension which enables the plug to be lodged in the sinus tarsus but not pass therethrough.

Before inserting the selected plug, Keith needles may be provided on the ends of the lines or sutures 32, 32a, 32b, 32c or 32d. These needles should then be carefully passed through the sinus tarsus 26 utilizing only digital pressure. If such an instrument is used to insert the needles it is possible to actually pass the needles through the cartilagenous bone. This should not be done.

The medial exit should lie as cephalad as possible, and if meticulously done the line ends such as ends 32 can be consistantly passed above the posterior tibial tendon 36 in FIG. 2. After one needle has been passed, the other Keith needle is passed parallel to the first, with the line end 32 exiting approximately 2-3 mm. from the first to insure that a portion of the deltoid ligament is incorporated. Care should be taken in not criss-crossing the ends 32 as they are passed through the sinus tarsi and then are tied, as this will result in imporper seating of the implant plug 30.

A skin incision between the two needles allows the knot 37 to be tied over i.e., on the outer side of the deltoid ligament 36 with the foot 10 held in the supinated position. Prior to cutting the line 32 the foot 10 is promated to check once again for stability and seating of the implant plug 30 as well as correction of the table. (One cannot overemphasize the care in avoiding the neurovascular bundle in the medial aspect of the foot.) The sutures or lines 32 medialy are then cut and the capsule is closed utilizing preferrably 3-0 DEXON and the subcutaneous tissue closed utilizing preferrably 4-0 DEXON. The skin is sutured utilizing 5-0 stainless steel wire in a subcuticular suture.

Short casts (not shown) are applied to the leg of the patient while the patient is under general anesthesia and while the foot 10 is held in the neutral position and the malleoli are cupped to reduce slipping of the casts. Follow up:

The short leg cast is left in place for two weeks without placing any activity restrictions on the patient. Casting may not be absolutely necessary, but I believe that immobilization of and protecting the foot from external trauma for the initial stages of wound healing outweighted the disadvantages of casting. Since tendo achilles lengthenings, gastrocnemius recessions, etc., have been used in conjunction with this procedure, the cast is to be left in place for the appropriate amount of time required by the additional procedures. When the cast is removed the foot is to be redressed and the wire suture removed.

Subjective results have shown 94% of the patients reported a 50% or better improvement in their flat foot. Objective findings revealed substantial reduction in both the talocalcaneo angle (Kite's angle), and declination angle of the talus. The two most significant changes in the procedure of the present invention, as compared to other procedures include preshaping and sizing the implant plug 30 for selection of an appropriate size by insertion in the tarsal sinus and assuring that implant will remain in place by providing a securing means connected over the deltoid ligament namely the non-absorbable sutures or lines 32. This effectively eliminated the problem of the implant extruding from the tarsal sinus 26.

I claim:

1. A process of correcting pes plano valgus comprising the steps of preparing a prosthesis by producing a unitary biocompatible plastic plug having a major base, a minor base and a tapered conical sidewall, tapering from said major base to said minor base and securing flexible lines to said plug so that the lines extend from said minor base, exposing the sinus tarsus of a persons's foot, inserting the lines and said plug, minor base first into the subtalar opening between the talus and calcaneous bones of said foot so that said plug is disposed within the sinus tarsus of said foot, continuing the insertion of said lines through said subtalar so that said lines pass above the posterior tendon and thence around opposite portions of the deltoid ligament, adjacent to said sinus tarsus and thereafter tying the end portions of said lines together, sufficiently close to said deltoid ligament that the lines restrain said plug within said sinus tarsus and prevent said plug from being forced outwardly therefrom, said plug being sufficiently large that it does not pass through the sinus tarsus but is wedged therein.

2. The process difined in claim 1 wherein said plug is selected from a group of different sized plugs selectively inserted into said sinus tarsus, said plug being sufficient in transverse dimension that is does not pass through said sinus tarsus.

3. The process defined in claim 1 including producing a plurality of plugs of different sizes, providing each of said plugs with a line embedded by an intermediate portion into said plug, the line having ends which protrude from the minor base of said plug, inserting selectively said plug into said sinus tarsus so as to determine which of said plugs will fit therein and, prior to the time that the line of the selected plug is passed around the deltoid ligament.

* * * * *